(12) United States Patent
Marleau

(10) Patent No.: US 9,151,852 B1
(45) Date of Patent: Oct. 6, 2015

(54) MATERIAL IDENTIFICATION BASED UPON ENERGY-DEPENDENT ATTENUATION OF NEUTRONS

(71) Applicant: Sandia Corporation, Albuquerque, NM (US)

(72) Inventor: Peter Marleau, Dublin, CA (US)

(73) Assignee: Sandia Corporation, Albuquerque, NM (US)

( * ) Notice: Subject to any disclaimer, the term of this patent is extended or adjusted under 35 U.S.C. 154(b) by 0 days.

(21) Appl. No.: 14/296,332

(22) Filed: Jun. 4, 2014

(51) Int. Cl.
- *G01T 1/20* (2006.01)
- *G01T 3/06* (2006.01)
- *G01V 5/00* (2006.01)
- *G01T 3/00* (2006.01)

(52) U.S. Cl.
CPC .............. *G01T 3/065* (2013.01); *G01T 3/005* (2013.01); *G01V 5/0008* (2013.01)

(58) Field of Classification Search
CPC ...... G01T 3/00; G01V 5/0091; G01V 5/0016; G01V 5/0008; G01V 5/104; G01V 5/0041; G01N 23/09; G01N 23/05; G01N 23/10; G01N 23/02; G01N 23/222
USPC ........................................................ 250/362
See application file for complete search history.

(56) References Cited

U.S. PATENT DOCUMENTS

| | | | |
|---|---|---|---|
| 7,622,709 B2 | 11/2009 | Zillmer et al. | |
| 7,649,977 B2 | 1/2010 | Johnson | |
| 2002/0171042 A1 | 11/2002 | Chen et al. | |
| 2007/0069145 A1* | 3/2007 | Leonhardt | 250/390.04 |
| 2009/0067574 A1* | 3/2009 | Johnson | 378/57 |
| 2009/0168958 A1* | 7/2009 | Cozzini et al. | 378/57 |
| 2012/0019510 A1* | 1/2012 | Bingham et al. | 345/419 |
| 2013/0056643 A1* | 3/2013 | Ziskin et al. | 250/390.02 |
| 2013/0264486 A1* | 10/2013 | Bingham et al. | 250/390.02 |
| 2014/0270034 A1* | 9/2014 | Clayton et al. | 376/154 |

OTHER PUBLICATIONS

Mor, et al., "High Spatial Resolution Fast Neutron Imaging Detectors for Pulsed Fast-Neutron Transmission Spectroscopy", IOP Publishing for SISSA, May 20, 2009, pp. 1-25.
Chen, et al., "Fast Neutron Resonance Radiography for Elemental Imaging: Theory and Applications", IEEE Transactions on Nuclear Science, vol. 49, No. 4, Aug. 2002, pp. 1919-1924.
Sowerby, et al., "Recent Developments in Fast Neutron Radiography for the Interrogation of Air Cargo Containers", IAEA Conference, May 4-8, 2009, pp. 1-15.
Chadwick, et al., "Next Generation Evaluated Nuclear Data Library for Nuclear Science and Technology", Nuclear Data Sheets 107, 2006, pp. 1-130.

* cited by examiner

*Primary Examiner* — David J Makiya
*Assistant Examiner* — Taeho Jo
(74) *Attorney, Agent, or Firm* — Medley, Behrens & Lewis, LLC

(57) ABSTRACT

Various technologies pertaining to identifying a material in a sample and imaging the sample are described herein. The material is identified by computing energy-dependent attenuation of neutrons that is caused by presence of the sample in travel paths of the neutrons. A mono-energetic neutron generator emits the neutron, which is downscattered in energy by a first detector unit. The neutron exits the first detector unit and is detected by a second detector unit subsequent to passing through the sample. Energy-dependent attenuation of neutrons passing through the sample is computed based upon a computed energy of the neutron, wherein such energy can be computed based upon 1) known positions of the neutron generator, the first detector unit, and the second detector unit; or 2) computed time of flight of neutrons between the first detector unit and the second detector unit.

20 Claims, 10 Drawing Sheets

MATERIAL IDENTIFICATION BASED UPON ENERGY-DEPENDENT ATTENUATION OF NEUTRONS

STATEMENT OF GOVERNMENTAL INTEREST

This invention was developed under Contract DE-AC04-94AL85000 between Sandia Corporation and the U.S. Department of Energy. The U.S. Government has certain rights in this invention.

BACKGROUND

Interest in screening capabilities has resulted in significant investment in thermal neutron analysis (TNA) and fast neutron analysis (FNA), which probe the nuclear structure of matter, rather than the electronic structure of matter as x-ray-based devices do. With more specificity, x-ray devices are sensitive only to variations in density, and thus fail to provide effective identification when materials include certain (light) elements. In TNA, gamma particles resulting from thermal neutron capture reactions in materials of interest (hydrogen and nitrogen) are used in connection with identifying certain materials. FNA is a far more powerful technique and measures either the gamma rays from nuclei activated by a neutron beam or the energy of an attenuated neutron beam.

Pulsed fast neutron analysis (PFNA) has been utilized to perform two-dimensional elemental imaging. This technology, however, requires complex optics and employs a time-of-flight (ToF) technique combined with sophisticated high-flux pulsed accelerator technology to determine neutron energies. These pulsed systems tend to be relatively expensive, prohibiting widespread use.

SUMMARY

The following is a brief summary of subject matter that is described in greater detail herein. This summary is not intended to be limiting as to the scope of the claims.

Various technologies pertaining to material identification are described herein. Also described herein are various technologies pertaining to generating a volumetric image, wherein voxels in the volumetric image have values that are indicative of elements represented in the voxels. With more particularity, material identification can be performed by measuring energy-dependent attenuation of neutrons having a range of energies (e.g., 1-13 MeV) as such neutrons pass through a sample of interest. In an exemplary embodiment, information pertaining to elemental composition of the sample can be ascertained based upon resonances in the energy-dependent elastic scattering cross sections (energy-dependent resonances) of neutrons that are directed to the sample, wherein an energy-dependent resonance is unique to a particular element. Given sufficient energy resolution, unique energy-dependent resonances in the energy dependent attenuation for a sample can be used to identify a wide range of materials in the sample. Accordingly, the technology described herein can be utilized in connection with discriminating between explosives, illicit drugs, etc.

An exemplary system that is configured to perform material identification and imaging based upon energy-attenuated neutrons includes a mono-energetic neutron generator. Furthermore, such neutron generator may be non-pulsed, thereby allowing for the system to include an off-the-shelf (OTS) neutron generator. A first detector is included in the system, wherein a position of the first detector relative to the neutron generator is known. The system further includes a second detector, wherein position of the second detector relative to the first detector is known. At least one electronic circuit, which may be an application-specific integrated circuit (ASIC), field programmable gate array (FPGA), general-purpose processor (CPU), etc., is in communication with the first detector and the second detector. A sample that is to be analyzed is positioned between the first detector and the second detector.

In operation, the neutron generator is caused to (isotropically) emit neutrons having a known energy (e.g., 14 MeV). The first detector is impacted by neutrons emitted from the neutron generator, wherein the interaction of the neutrons with the detector causes the neutrons to be elastically down-scattered in energy (as well as scattered spatially). Neutrons emitted by the first detector have energies over a relatively wide range (e.g., 1 MeV-13 MeV).

Further, responsive to a neutron impacting the first detector, the first detector outputs a signal, wherein the electronic circuit receives the signal from the first detector. The electronic circuit generates a time-tag that indicates a time when the neutron impacted the first detector. The electronic circuit can thereafter interrogate the second detector based upon the time-tag generated by the electronic circuit. With more specificity, as the position of the second detector relative to the first detector is known, a time window in which the neutron emitted from the first detector will impact the second detector (if such neutron impacts the second detector) is also known. Thus, the electronic circuit can perform time gating such that the electronic circuit interrogates the second detector only in the time window when the neutron is expected to impact the second detector. It is to be understood, however, that the time window does not restrict energy acceptance of the second detector, as the window is sufficiently large to allow for detection of neutrons corresponding to all energies expected based upon the down-scattering of neutron energies undertaken at the first detector.

The second detector outputs a signal responsive to the neutron impacting the second detector. The electronic circuit receives such signal (in the expected time window), and assigns a second time-tag responsive to receipt of the signal from the second detector. In an exemplary embodiment, the time tags can be used to reduce noise (e.g., reject backgrounds caused by room scatter, accidental coincidences between different neutrons, . . . ). Based upon known geometry of the overall system (the known position of the first detector relative to the neutron generator, and the known position of the second detector relative to the first detector), and further based upon data collected when the sample is not positioned between the first detector and the second detector, energy-dependent attenuation caused by the sample can be ascertained. The operation of the system can be repeated for multiple pairs of detectors and multiple neutrons, such that the sample is scanned over a relatively wide range of energies. Based upon computed attenuation as a function of energy, elemental composition of the sample can be identified (e.g., by comparing the measured energy dependent attenuation with energy dependent elastic cross section signatures for particular elements). In another exemplary embodiment, a volumetric image of the sample can be generated, wherein the volumetric image is indicative of a spatial distribution of elements throughout the sample.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

DETAILED DESCRIPTION

Figure 1:
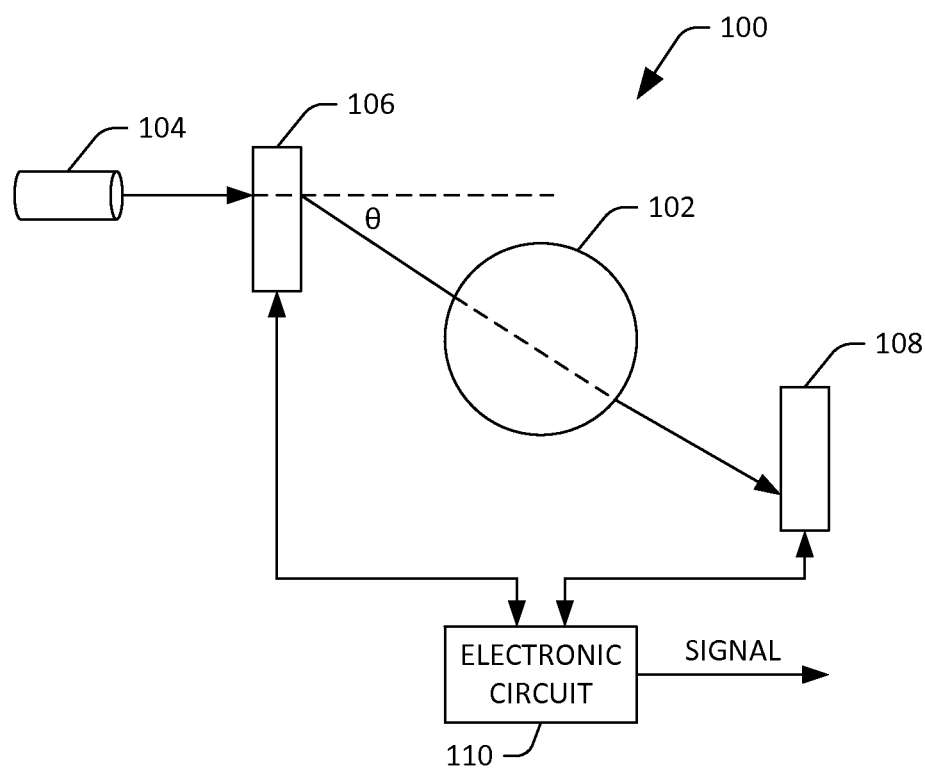
FIG. 1 is a functional block diagram of an exemplary system that facilitates identifying material in a sample and/or imaging the sample based upon neutron energy dependent attenuation.

Various technologies pertaining to identifying materials of a sample are now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects. Further, it is to be understood that functionality that is described as being carried out by certain system components may be performed by multiple components. Similarly, for instance, a component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form. Additionally, as used herein, the term "exemplary" is intended to mean serving as an illustration or example of something, and is not intended to indicate a preference.

With reference now to FIG. 1, a functional block diagram of an exemplary system 100 that facilitates identifying materials in a sample 102 and/or generating a volumetric image of the sample 102 is illustrated. The system 100 comprises a mono-energetic neutron generator 104. In an exemplary embodiment, the neutron generator 104 can emit neutrons having an energy of approximately 14.1 MeV, and can emit such neutrons isotropically. The system 100 further includes a first detector unit 106 that is configured to generate a signal responsive to a neutron impacting the first detector unit 106. A position of the first detector unit 106 relative to a position of the neutron generator 104 is known. As will described herein, the first detector unit 106 can comprise a scintillator that generates an optical signal responsive to being impacted by the neutron. The first detector unit 106 comprises componentry that converts the optical signal into an electrical signal, and the first detector unit 106 outputs the electrical signal.

The system 100 further comprises a second detector unit 108 positioned on an opposing side of the sample 102 relative to the first detector unit 106. A position of the second detector unit 108 relative to the position of the first detector unit 106 is also known. The second detector unit 108 is configured to detect a neutron; thus, the second detector unit 108 outputs an electrical signal responsive to the neutron impacting, for example, a scintillator of the second detector unit 108.

The system 100 further optionally comprises an electronic circuit 110 that is in communication with the first detector unit 106 and the second detector unit 108. While shown as being a single circuit, it is to be understood that the electronic circuit 110 can represent multiple electronic circuits. As will be described in greater detail herein, the electronic circuit 110 is generally configured to receive electrical signals output by the first detector unit 106 and the second detector unit 108, respectively, and output a signal that is indicative of a material included in the sample 102 based upon the electrical signals received from the detector units 106 and 108. In another exemplary embodiment, events detected by the detector units 106 and 108 can be recorded and analyzed by an external circuit (e.g., paired (double scatter) events may be pieced together at a later point in time). The system 100 may be particularly well-suited in connection with detecting explosives, illicit drugs, contraband, etc.

An exemplary operation of the system 100 is now set forth. The neutron generator 104 emits neutrons from a known position relative to the first detector unit 106. As shown in FIG. 1, a neutron output by the neutron generator 104 can impact the scintillator of the first detector unit 106, and the first detector unit 106 can output a first electrical signal responsive to the neutron impacting the scintillator therein. The electronic circuit 110 can receive the first electrical signal from the first detector unit 106, and can generate time-tag for the neutron that identifies a point in time when the neutron was detected by the first detector unit 106. Subsequent to interacting with the scintillator of the first detector unit 106, the neutron may exit the first detector unit 106 at a particular angle (θ) relative to the direction of the neutron when emitted by the neutron generator 104. Such angle θ is indicative of an energy of the neutron when exiting the first detector unit 106. Neutrons that impact the first detector unit 106 are spatially redirected and downscattered in energy. Thus, neutrons exiting the first detector unit 106 can have energies over a relatively wide range (e.g., 1 MeV-13 MeVs).

Referring again to the single neutron, the electronic circuit 110 can process electrical signals from the second detector unit 108 based upon the first electrical signal received from the first detector unit 106. For example, as the position of the neutron generator 104 relative to the first detector unit 106 is known, and as the position of the second detector unit 108 relative to the first detector unit 106 is known, a time window within which the neutron will impact the second detector unit 108 (if the neutron impacts the second detector unit 108) can also be known. Thus, the electronic circuit 110 can be gated such that a second electrical signal output by the second detector unit 108 is only processed if the second detector signal is received by the electronic circuit 110 within the above-mentioned time window. When the sample 102 is positioned between the first detector unit 106 and the second detector unit 108, the neutron may pass through the sample 102 or may be scattered, such that the path of the neutron is altered (and the neutron will not impact the second detector unit 108). If, however, the neutron is not scattered, the neutron may be detected by the second detector unit 108 in the time window.

Thus, it can be ascertained that when the sample 102 is present between the first detector unit 106 and the second detector unit 110, fewer neutrons will be detected at the second detector unit 110 (along the path between the first detector unit 106 and the second detector unit 108) when compared to a number of neutrons detected by the second detector unit 108 (along such path) when there is no sample between the first detector unit 106 and the second detector unit 108. The energy-dependent neutron attenuation caused by the presence of the sample 102 can be used to identify at least one element in the sample 102.

With still more specificity, in a calibration phase, the system 100 can be operated without the sample 102 positioned between the first detector unit 106 and the second detector unit 108. The neutron generator 104 is caused to emit neutrons, and the first detector unit 106 elastically downscatters the neutrons in energy. Due to the known geometry of the system 100, energy of neutrons that exit the first detector unit 106 and that travel the path shown in FIG. 1 is known. If the geometry happens to be unknown, or spatial resolution is poor, ToF data pertaining to neutrons that exit the first detector unit 106 and impact the second detector unit 108 can be ascertained, and such ToF data can be used to determine energy of neutrons that travel the path shown in FIG. 1. The rate at which neutrons travelling the illustrated travel path between the first detector unit 106 and the second detector unit 108 can be retained as a baseline (this process can be repeated for numerous travel paths between numerous detector unit pairs).

When the sample 102 is placed between the first detector unit 106 and the second detector unit 108, the process noted above is repeated. When the sample 102 is present, however, the second detector unit 108 may detect neutrons exiting the first detector unit 106 and travelling the illustrated travel path at a different rate compared to the rate of detection along the travel path when the sample 102 is not present. The energy-dependent attenuation of neutrons caused by the sample 102 is indicative of at least one element of the sample 102. Additionally, as the travel path of the neutron between the first detector unit 106 and the second detector unit 108 is known, when the system 100 is adapted to include several detectors positioned around the sample 102, the electronic circuit 110 can be configured to generate a volumetric image of the sample 102, wherein such volumetric image is indicative of spatial distribution of elements of the sample 102.

Figure 2:
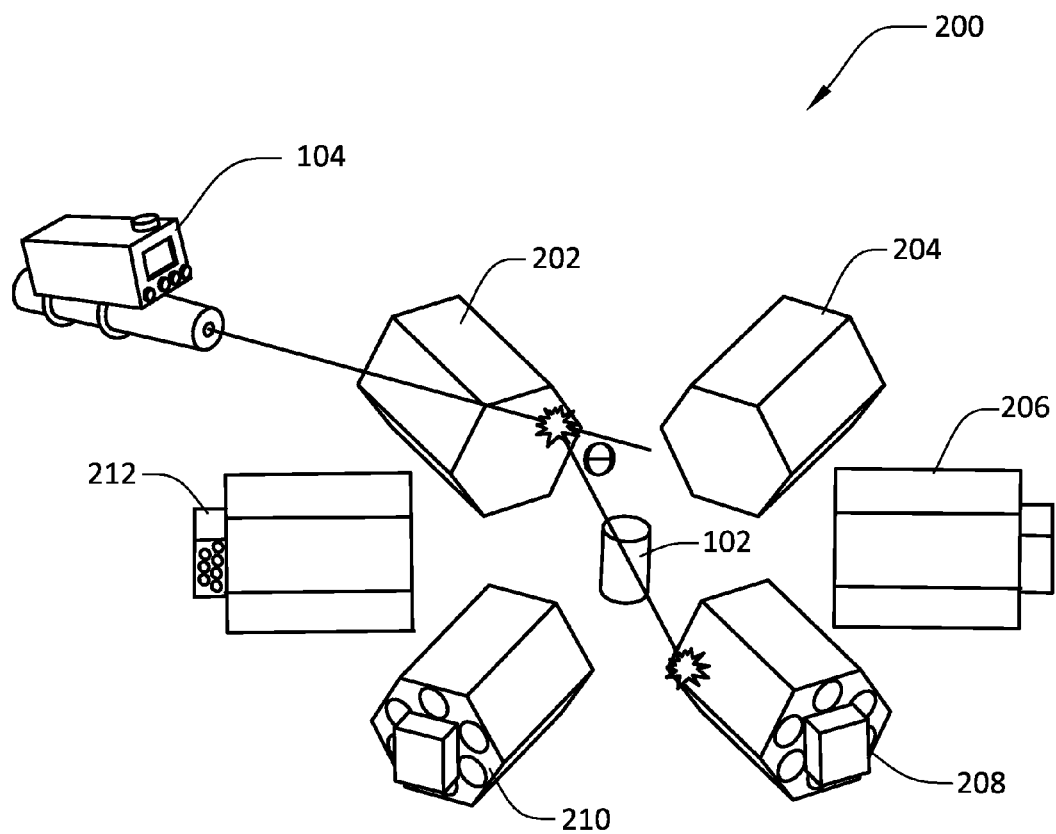
FIG. 2 illustrates an exemplary system that facilitates identifying materials in a sample and/or imaging the sample through utilization of multiple detector units surrounding the sample.

Now referring to FIG. 2, another exemplary system 200 that facilitates identifying elemental composition of the sample 102 and/or generating a volumetric image of the sample 102 is illustrated. The system 200 comprises the neutron generator 104, which emits neutrons. As indicated above, the neutron generator 104 can be a mono-energetic neutron generator, and further need not be a fast-pulse generator. The system 200 further comprises a plurality of detectors 202-212 that are positioned to surround the sample 102. Positions of each of the detectors 202-212 relative to the neutron generator 104 and positions of the detectors 202-212 relative to each other can be known. In an exemplary embodiment, the system 200 can be employed to determine energy dependent attenuation of neutrons that exit a detector unit with a relative wide range of energies (e.g., 1-13 MeV), wherein such attenuation is caused by the neutrons passing through the sample 102.

Figure 7:
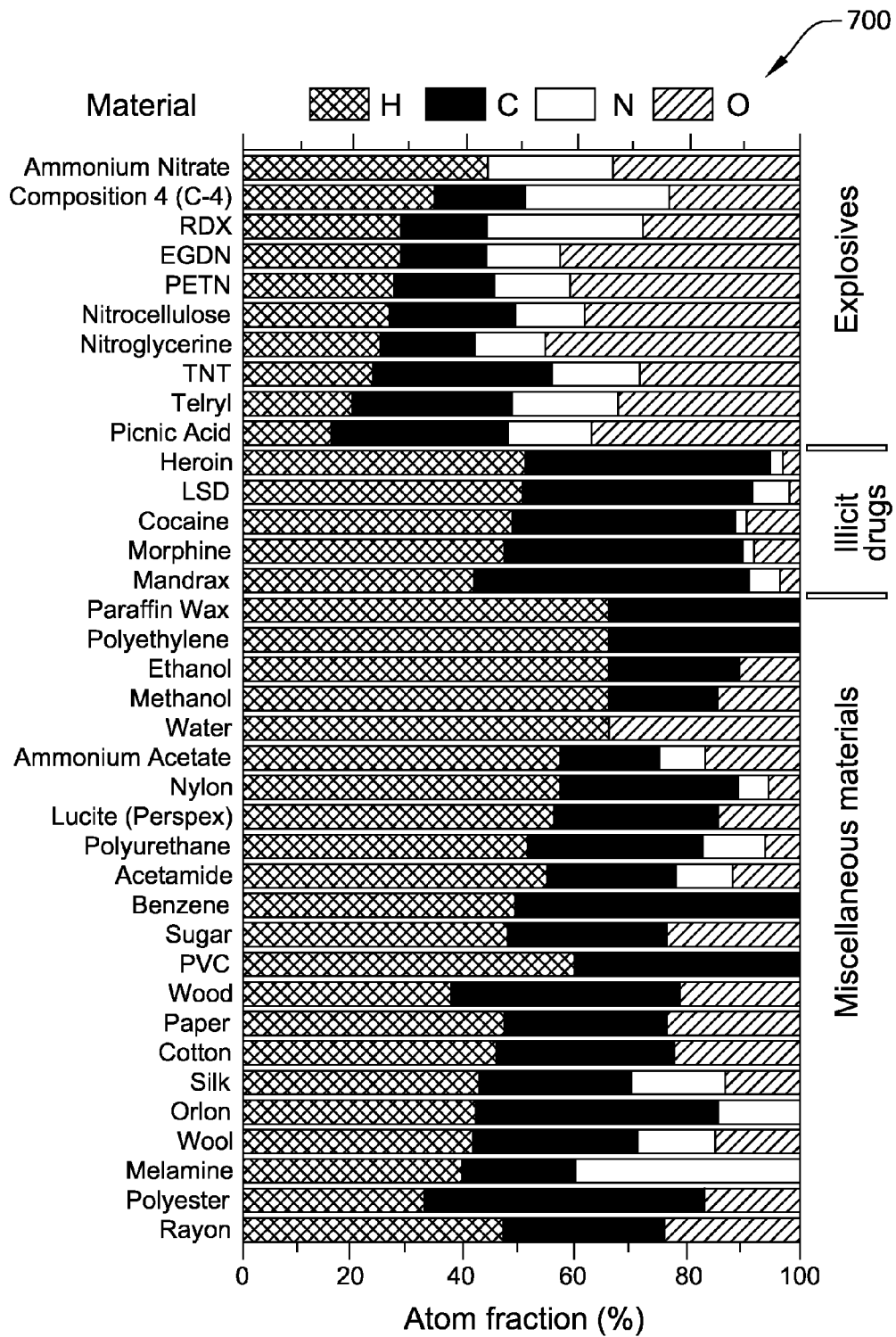
FIG. 7 is illustrates exemplary elemental composition of a plurality of materials.
Figure 8:
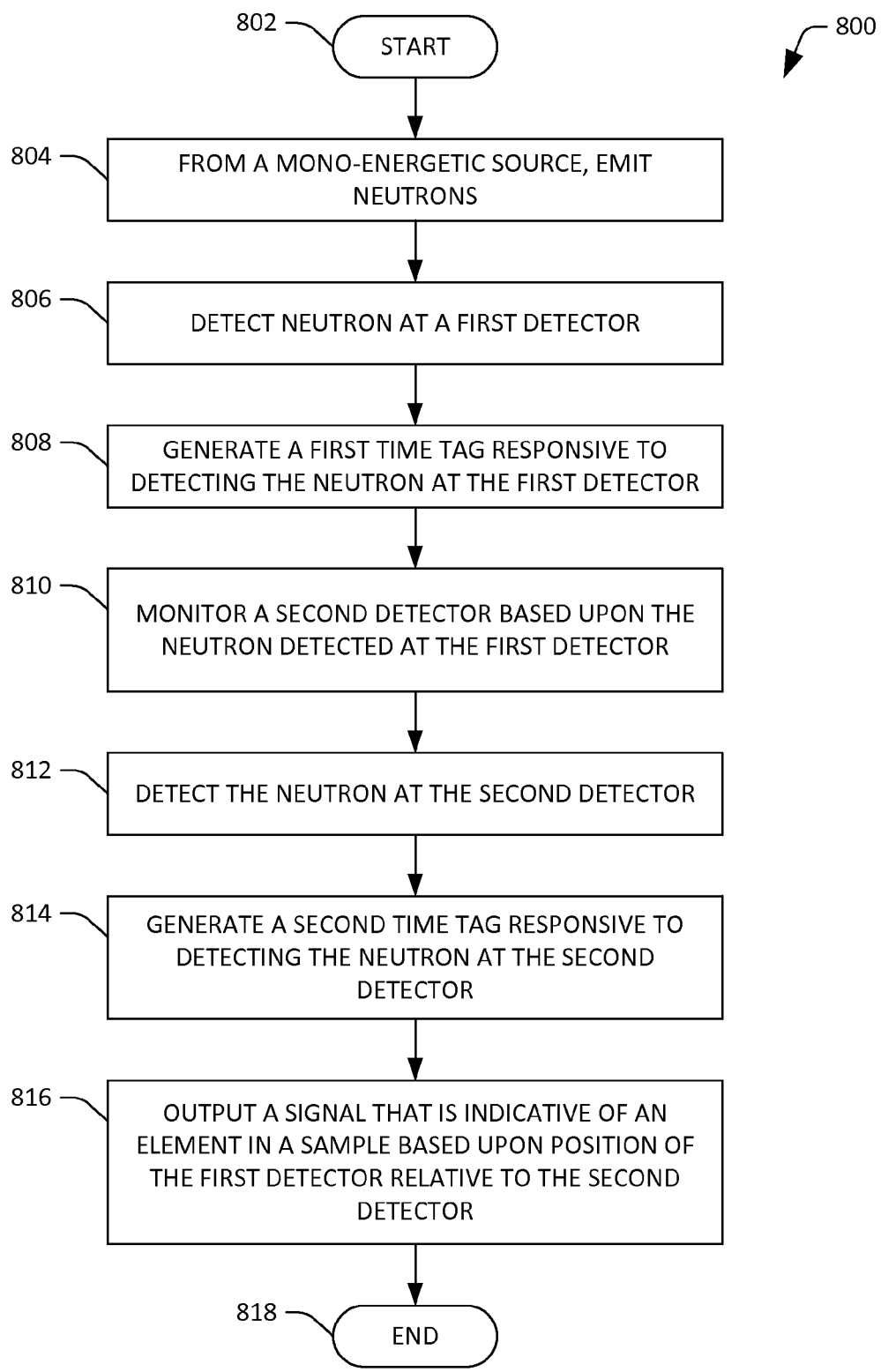
FIG. 8 is a flow diagram illustrating an exemplary methodology for identifying a material in a sample of interest.

Elemental information pertaining to the sample 102 can be determined from the neutron absorption resonances unique to each element in the sample 102. Referring briefly to FIG. 7, an exemplary spectrum of neutron interaction cross-sections for hydrogen, carbon, nitrogen, and oxygen, is illustrated. Given sufficient energy resolution, the unique resonances in the energy attenuation of the sample 102 can be used to categorize a wide range of materials. For example, this can serve as technique for discriminating between explosives, illicit drugs, and other materials. FIG. 8 depicts the atomic fraction of hydrogen, carbon, nitrogen, and oxygen for several materials of interest, along with common benign materials. Many conventional explosives, for example, are characterized by their relatively high nitrogen and oxygen content. It is understood that the technologies described herein, however, are not limited to the detection of the elements depicted in FIGS. 7 and 8.

Returning to FIG. 2, as noted above, the system 200 can be configured to downscatter and time tag neutrons through utilization of detector units. Accordingly, ToF measurements can be acquired without the neutron generator 104 emitting (fast) pulsed neutron beams. In the example shown in FIG. 2, neutrons emitted by the neutron generator 104 impact the first detector unit 202 (and other detector units). The first detector unit 202 downscatters neutrons in energy by an amount that is dependent upon the angle θ between the direction of the neutron when emitted by the neutron generator 104 and the direction of the neutron as it exits the first detector unit 202. For example, if neutrons emitted by the neutron generator 104 have an energy of 14.1 MeV, then the energy of the neutron exiting the first detector unit 202 is as follows:

$$E_i = \frac{14.1 \text{ MeV}}{1 + \tan^2\theta}, \tag{1}$$

where $E_i$ is the energy of the neutron exiting the first detector unit 202 (e.g., the energy of the neutron that is incident on the sample 102). For instance, $E_i$ can span a range from 0-14 MeV depending upon the scattering angle; accordingly, multiple energies interrogate the sample 102 simultaneously, vastly improving the required scan time for each sample. FIG. 2 depicts an exemplary path of a down-scattered neutron. The energy of the neutron when detected at the fourth detector unit 208 (as shown in FIG. 2) can also be represented as follows:

$$E_i = \frac{m}{2}\left(\frac{d}{t}\right)^2, \tag{2}$$

where d is the distance between a location of interaction in the first detector unit 202 and a location of interaction in the third detector unit 208, t is the time-of-flight of the neutron between the first detector unit 202 and the third detector unit 208, and m is the mass of the neutron. A difference between observed energy spectrums, with and without the sample present between the detectors 202-212, can provide a measure of energy dependent neutron attenuation attributed to the presence of the sample 102. An uncertainty in energy computed by the electronic circuit 100 (which can be in communication with the detectors 202-212) using Eq. (2) is a function of timing and/or spatial widths:

$$\sigma_{E_i} = \sqrt{\left(\frac{\partial E_i}{\partial d}\right)^2 \sigma_d^2 + \left(\frac{\partial E_i}{\partial t}\right)^2 \sigma_t^2} \quad (3)$$

or $$\sigma_{E_i} = \sqrt{\left(\frac{\partial E_i}{\partial d}\right)^2 \sigma_d^2} \quad (4)$$

$$= 2E_i \sqrt{\frac{\sigma_d^2}{d^2}}.$$

or $$\sigma_{E_i} = \sqrt{\left(\frac{\partial E_i}{\partial t}\right)^2 \sigma_t^2} \quad (5)$$

$$= 2E_i \sqrt{\frac{\sigma_t^2}{t^2}}.$$

Accordingly, timing and spatial resolution of the detector units 202-212 is directly related to the energy resolution that can be obtained. In addition, Eq. (1) can be used to measure the energy and/or to constrain the ToF to a range corresponding to the expected energies in order to reduce accidental backgrounds. If Eq. (1) is employed to determine the energy, the uncertainty can be given as follows:

$$\sigma_{E_i} = \sqrt{\left(\frac{\partial E_i}{\partial \theta}\right)^2 \sigma_\theta^2 + \left(\frac{\partial E_i}{\partial \alpha}\right)^2 \sigma_\alpha^2} \quad (6)$$

$$= 2\sqrt{2} \, E_i \tan\theta \sqrt{\left(\frac{z}{x^2+z^2}\right)^2 \sigma_x^2 + \left(\frac{-x}{x^2+z^2}\right)^2 \sigma_z^2 + \sigma_\alpha^2}, \quad (7)$$

where $\alpha$ is an angle defined by the angular extent of the emission region of the neutron generator 104 and z and x are the coordinates, for example, of the fourth detector unit 208 relative to the first detector unit 202.

As shown in FIG. 2, the detectors 202-212 are arranged cylindrically about the sample 102, wherein the cylinder has a known radius (e.g., approximately 50 cm). Further, in an exemplary embodiment, the detector units 202-212 can be on a same plane as the sample 102. The neutron generator 104, which may be a deuterium-tritium neutron source, can be situated outside of the cylindrical region formed by the detector units 202-212. For instance, the neutron generator 104 can be positioned some distance from a closest detector unit (e.g., the first detector unit 202). In an exemplary embodiment, such distance can be at least 1 m.

The three nearest detector units to the neutron generator 104 (units 202, 210, and 212) can be configured to initially receive neutrons emitted from the neutron generator 104 and downscatter such neutrons in energy. For example, the detector units 202, 210, and 212 can be referred to as "near units", and the detector units 204, 206, and 208 can be referred to as "far units". As noted above, neutrons emitted by the neutron generator 104 can have an energy of about 14.1 MeV. Neutrons that impact the first detector unit 202 are elastically downscattered in energy in such first detector unit 202 to, for instance, between 1 MeV and 13 MeV. The neutrons exiting the first detector unit 202 can be registered by the far units 204, 206, and 208 after such neutrons have passed through the sample 102. The known spatial positions of the neutron generator 104, the first detector unit 202, and the far units 204-208 can be used to compute an energy of a neutron detected at a far unit. In another exemplary embodiment, a time between the first detector unit 202 detecting a neutron and one of the far units 204-208 detecting the neutron can be used to measure the energy of the neutron detected at the far unit. As will be shown below, the electronic circuit 110 can include a trigger that is constructed from a 250 ns coincidence of any near unit with any far unit. Using Eq. (4), the uncertainty in the energy of neutrons passing through the sample 102 at 3 MeV can be approximately 2%. Pursuant to an example, when ToF data is used to compute the energy of a neutron, timing resolution may be a dominant factor contributing to the error. Geometrical constraints represented in Eq. (6), which depend only on the spatial resolution and separation of the detector units 202-212, can give an uncertainty in energy of approximately 1%.

Additionally, as indicated above, the system 200 can be employed to generate a volumetric image of the sample 102. Conventional three-dimensional imaging systems require rotation of the sample 102 with respect to a detector to provide multiple two-dimensional maps. The system 200 can generate a three-dimensional, volumetric image of the sample 102 with a single scan due to the multiple scattering angles of the neutrons incident on the sample 102. Elemental three-dimensional maps can be determined by measuring the complete energy dependent attenuation through paths between detector units. Total attenuation along each path can be the product of attenuation through each voxel along the path in the sample 102. By sampling every voxel, multiple times by different paths at different angles, the energy (elemental) and position dependence can be de-convolved to construct an elemental density map of the target space. Only attenuation between pairs of near and far units may be considered.

Figure 3:
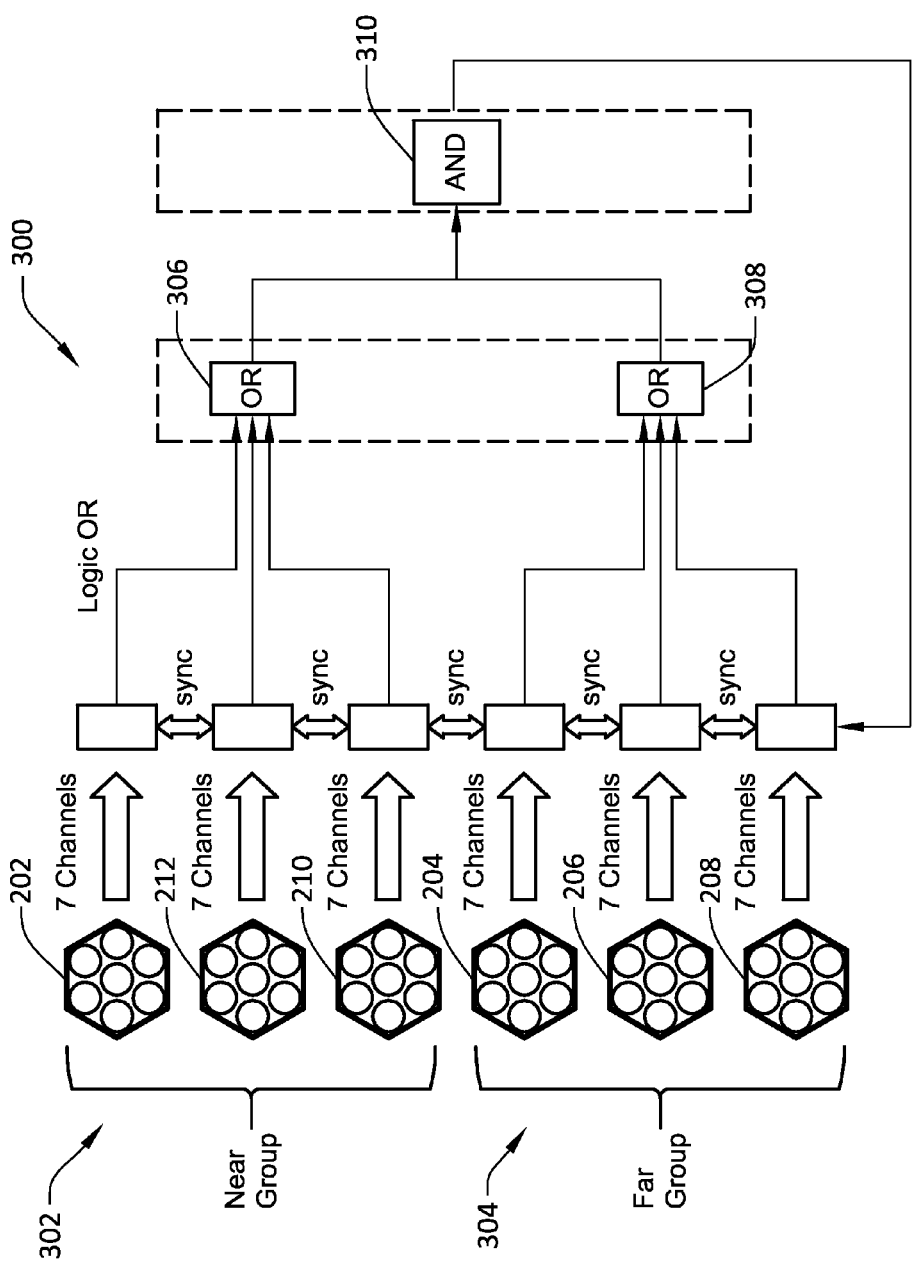
FIG. 3 illustrates an exemplary trigger scheme for use with the exemplary system shown in FIG. 2.

Now referring to FIG. 3, a schematic diagram 300 of an exemplary trigger scheme that can be employed in connection with the system 200 is illustrated. The trigger scheme indicates that each detector unit has seven separate channels, each of which can output a signal that indicates that the detector has been impacted by a neutron and position on the detector unit of the impact. As noted above, detectors are separated into a near group 302 and a far group 304, wherein the near group 302 includes the detector units 202, 212, and 210, and the far group includes the detector units 204, 206, and 208. The channels of each of the detector units 202-212 can be multiplexed and synchronized in time with one another. The outputs of detector units in the near group are provided to an OR gate 306, while the outputs of the detector units in the far group are provided to an OR gate 308. A coincidence of the logical OR gate 306 and the logical OR gate 308 can be approximately 250 nanoseconds, which can be set as the trigger condition. The output of the OR gates 306 and 308 is provided to an AND gate 310, wherein the output of the AND gate 310 can be utilized to synchronize the outputs of the detectors 202-212.

Figure 4:
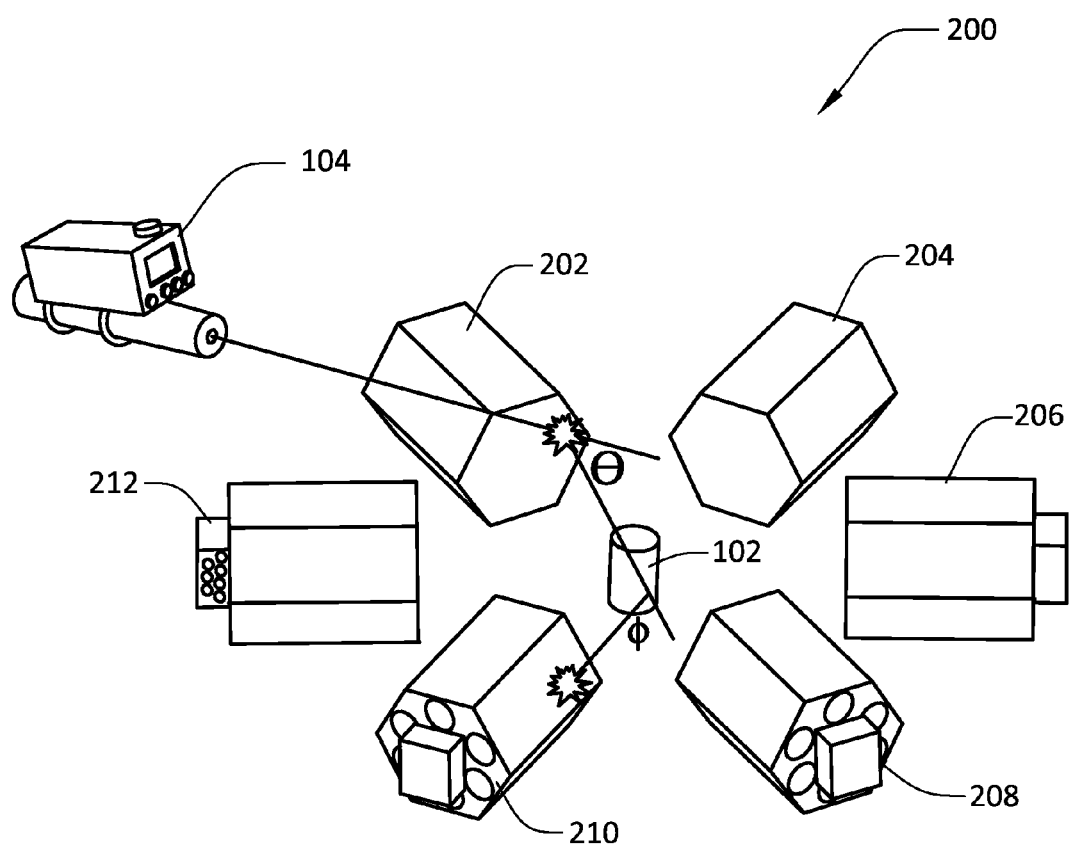
FIG. 4 illustrates an exemplary system that facilitates identifying materials in a sample and/or imaging the sample based upon detection of energy attenuation of neutrons.

Now referring to FIG. 4, another exemplary operation of the system 200 is depicted. For example, the system 200 can be configured to perform material identification, not just by the energy-attenuated neutron signal, but by a direct measurement of the mass of the scattered nuclei within the sample 102. For instance, if it is assumed that m<<M, energy lost by a neutron in an elastic scattering interaction can be given as follows:

$$Q = \frac{4mM}{(M+m)^2}\sin^2\frac{\phi}{2}, \quad (8)$$

where M and m are the masses of the scattered nucleus and neutron respectively, and φ is the angle of the scattered neutron in the sample 102. A measurement of the neutron energy before and after a collision along with trajectory information can uniquely determine the mass of the scattered nucleus as follows:

$$M = \frac{2m}{Q}\sin^2\frac{\phi}{2}\left(1\pm\sqrt{1-\frac{Q}{\sin^2\frac{\phi}{2}}}\right) - m, \quad (9)$$

where $Q=E_i-E_f$. The geometry of the componentry of the system 200 allows for energy and trajectory measurements to be made so long as the sample 102 is limited to approximately 1 scattering length of material, and adequate position and energy resolution of the neutron at all scattering locations is realized. A degree to which the mass of the scattered nuclei can be determined can depend upon the resolution of the energy loss, which is dependent upon the timing and spatial resolution. This exemplary operation of the system 200, however, adds a new channel of information on the sample 102, and can improve minimization routines.

Figure 5:
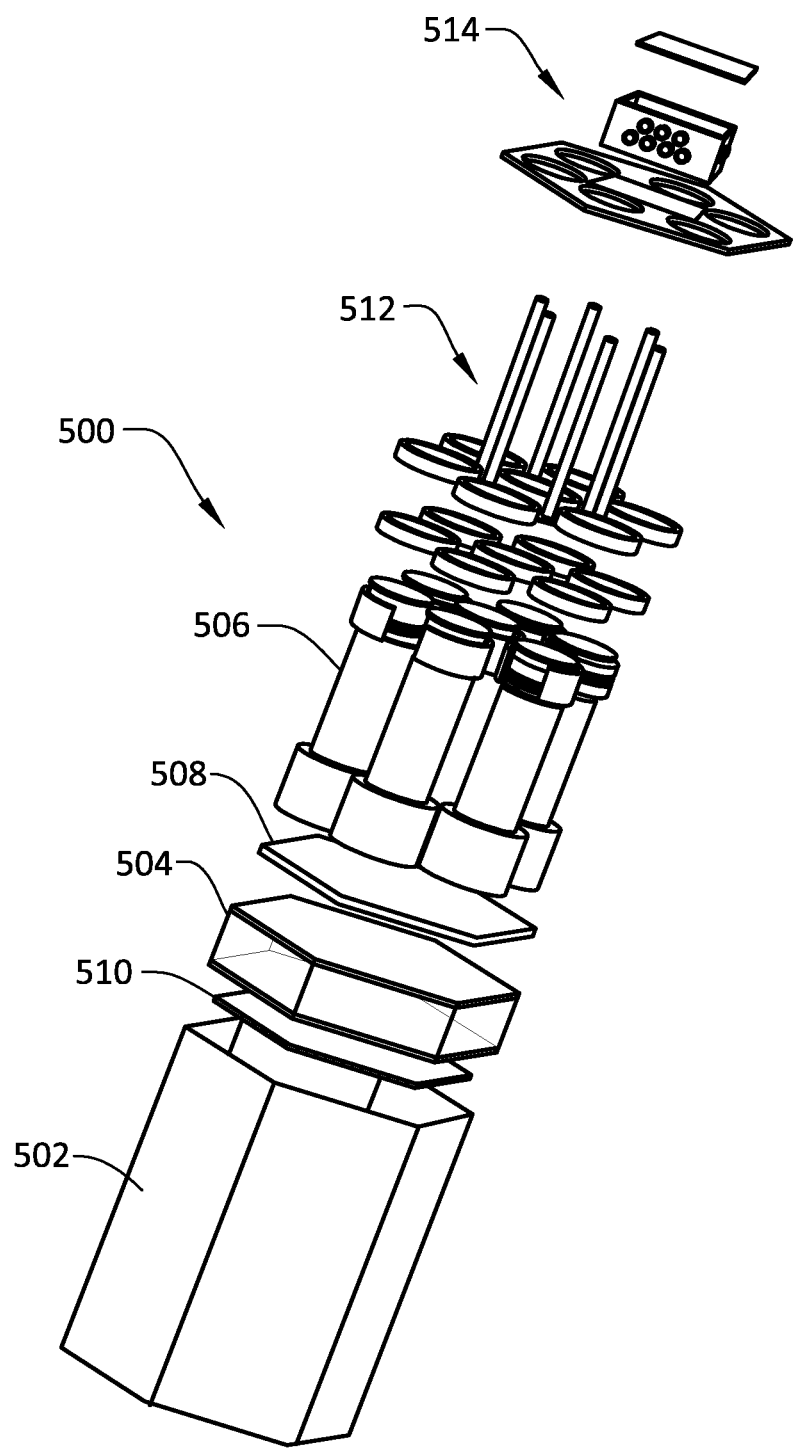
FIG. 5 is an exploded view of an exemplary detector unit.
Figure 6:
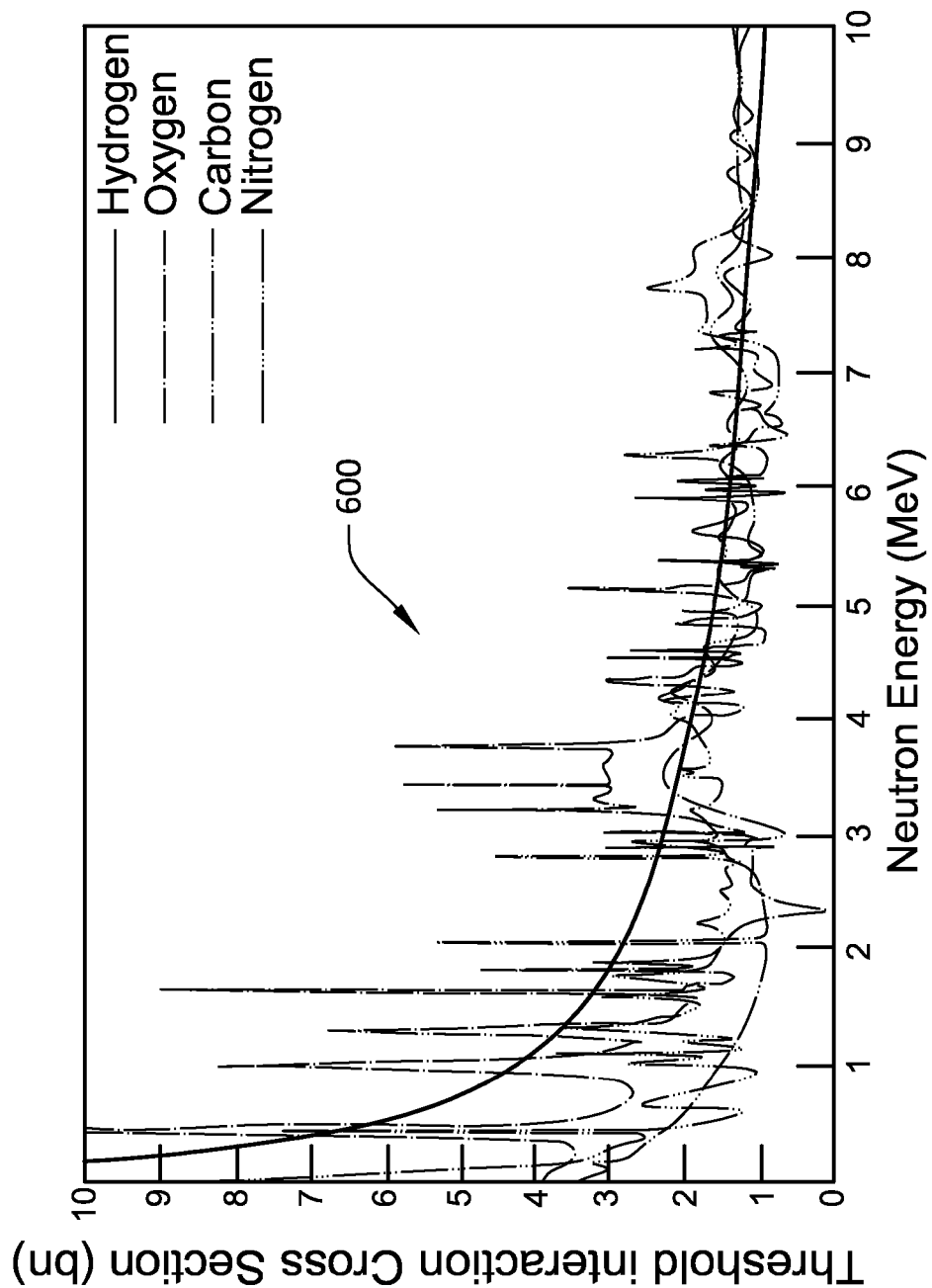
FIG. 6 is a graph that depicts exemplary signatures of a plurality of elements over a range of energies.

Now referring to FIG. 5, an exploded view of an exemplary detector unit 500, which can be utilized as any of the detector units 202-212 in the system 200, is illustrated. The detector 500 can include a protective cover 502, which can be composed of a plastic, a metal (such as aluminum), etc. The detector unit 500 further comprises a scintillator block 504, which can be composed of a scintillator crystal and have a thickness on the order of 2 inches. The detector 500 further comprises a plurality of photomultiplier tubes 506, which can be on the order of 7 inches in length. Sides of the scintillator block 504 can be coated with black absorbing paint and a face of the scintillator block 504 can be coated with a white reflective material to increase an amount of light collected. A waveguide 508 can be used in connection with coupling the scintillator block 504 with the photomultiplier tubes 506. An LED calibration board 510 can be utilized for position reconstruction calibrations. A plurality of holders 512 are configured to hold the photomultiplier tubes 506 in place, and a high voltage power supply 514 provides a bias voltage to the photomultiplier tubes 506. Position resolution of the detector 500 can be calculated using any suitable technique. In an exemplary embodiment, spatial resolution of approximately 0.4 cm (a) can be obtained. To determine timing resolution, responses to muons propagating perpendicularly to the photomultiplier tube faces can be used.

Figure 9:
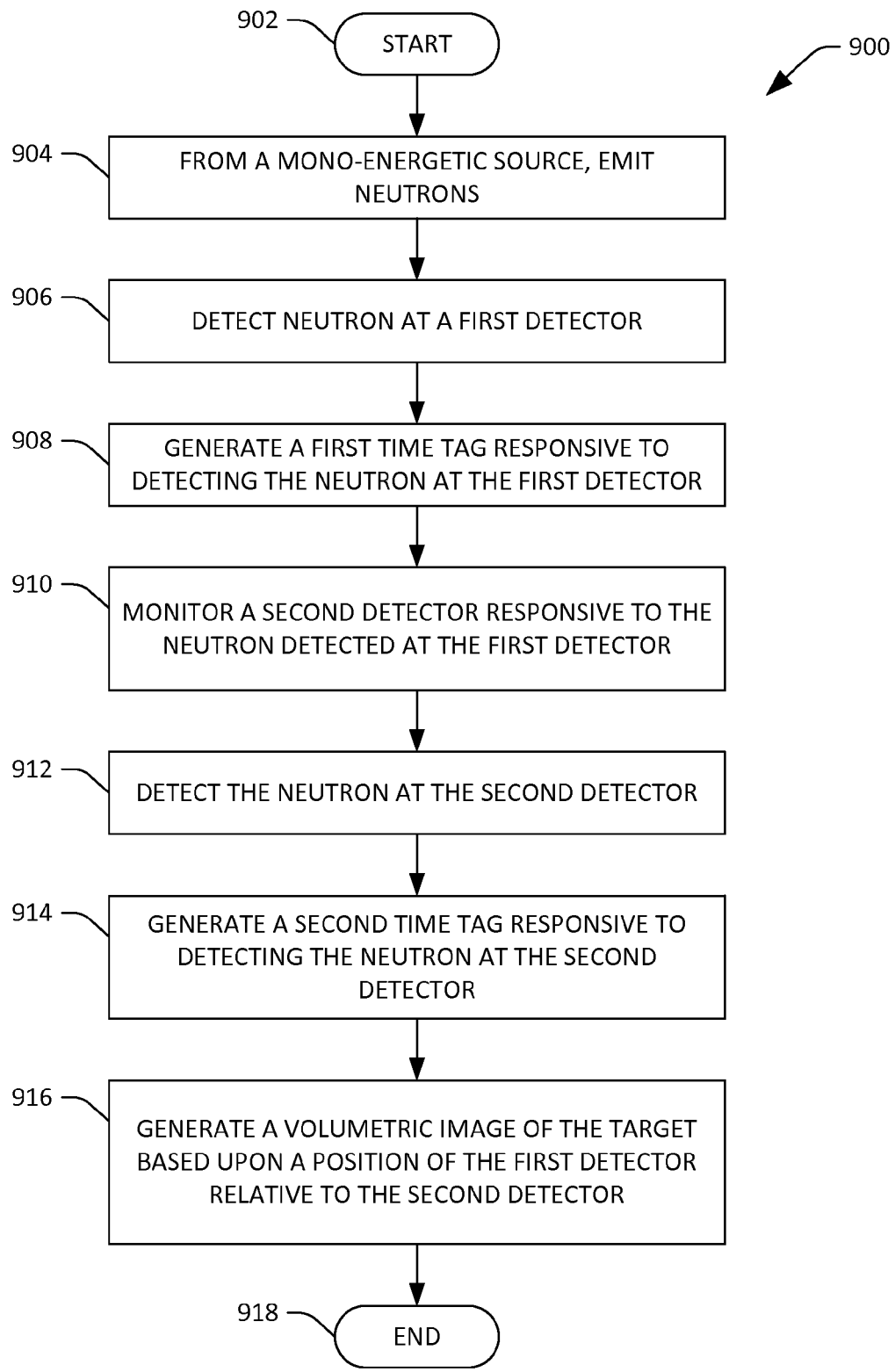
FIG. 9 is a flow diagram illustrating an exemplary methodology for generating a volumetric image of a sample based upon detected energy attenuation of neutrons.

FIGS. 8-9 illustrate exemplary methodologies relating to the identification of materials in a target of interest. While the methodologies are shown and described as being a series of acts that are performed in a sequence, it is to be understood and appreciated that the methodologies are not limited by the order of the sequence. For example, some acts can occur in a different order than what is described herein. In addition, an act can occur concurrently with another act. Further, in some instances, not all acts may be required to implement a methodology described herein.

Moreover, the one or more acts described herein may represent computer-executable instructions that can be implemented by one or more processors and/or stored on a computer-readable medium or media. The computer-executable instructions can include a routine, a sub-routine, programs, a thread of execution, and/or the like. Still further, results of acts of the methodologies can be stored in a computer-readable medium, displayed on a display device, and/or the like.

With reference now to FIG. 8, an exemplary methodology 800 that facilitates outputting a signal that is indicative of an element in a sample is illustrated. The methodology 800 starts at 802, and at 804 neutrons are emitted from a mono-energetic neutron source. At 806, a neutron from the mono-energetic neutron source is detected at a first detector. At 808, a time-tag is generated responsive to the neutron being detected at the first detector. The first detector generally down-scatters the neutron that impacts the first detector.

At 810, a second detector is monitored based upon the neutron detected at the first detector, wherein a sample is positioned between the first detector and the second detector. For example, the second detector can be monitored to ascertain if the second detector detects the neutron that was first detected by the first detector. At 812, the neutron is detected at the second detector. At 814, a second time-tag can be generated responsive to detecting the neutron at the second detector. Thus, a time-of-flight between the first detector and the second detector when the neutron passes through the sample can be ascertained. This time-of-flight can be indicative of the energy of the neutron. Such energy can, in turn, be indicative of existence of an element in the sample. In another exemplary embodiment, rather than using time tags to determine the energy of the neutron, known spatial positions of componentry can be used to determine the energy of the neutron, and the time information can be used to reduce noise. At 816, a signal is output that is indicative of the element in the target based upon energy dependent attenuation caused by the presence of the sample between the first detector and the second detector. The methodology 800 completes at 818.

Now referring to FIG. 9, an exemplary methodology 900 that facilitates generating a volumetric image of a sample that is indicative of elemental composition of the sample is illustrated. The methodology 900 starts at 902, and at 904 neutrons are emitted from a mono-energetic neutron source. At 906, a neutron is detected at a first detector. At 908, a first time-tag is generated responsive to detecting the neutron at the first detector. At 910, a second detector is monitored based upon the neutron being detected at the first detector, wherein the sample is positioned between the first detector and the second detector. For instance, the second detector can be monitored in a time window that beings a threshold amount of time subsequent to the first detector detecting the neutron.

At 912, the neutron is detected at the second detector. Further, at 914, a second time-tag is generated that indicates when the second detector detected the neutron. As noted above, such second time-tag can be used to compute energy of the neutron and/or in connection with reducing noise. At 916, a volumetric image of the sample is generated based upon a position of the first detector relative to the second detector (and/or the time-of-flight of the neutron computed based upon the first time-tag and the second time-tag). The methodology 900 completes at 918.

Figure 10:
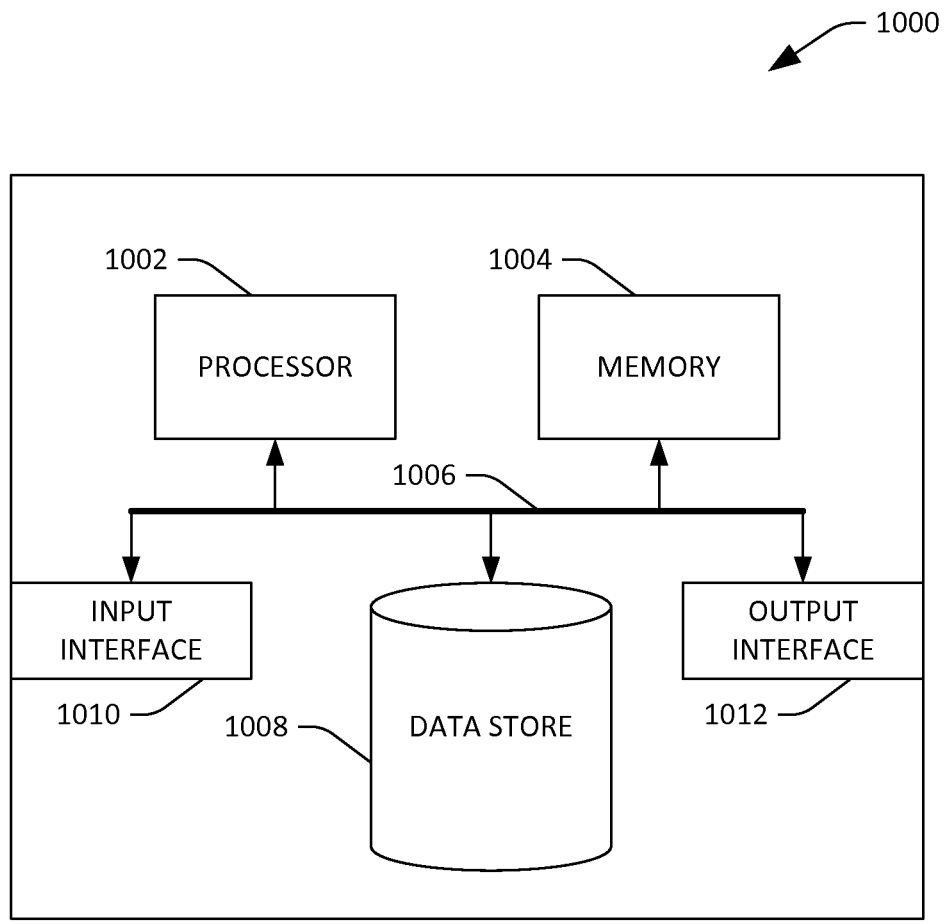
FIG. 10 is an exemplary computing system.

Referring now to FIG. 10, a high-level illustration of an exemplary computing device 1000 that can be used in accordance with the systems and methodologies disclosed herein is illustrated. For instance, the computing device 1000 may be used in a system that supports computing time-of-flight of a neutron between detector units. By way of another example, the computing device 1000 can be used in a system that computes energy-dependent attenuation of neutrons caused by a sample through which the neutrons pass. The computing device 1000 includes at least one processor 1002 that executes instructions that are stored in a memory 1004. The instructions may be, for instance, instructions for implementing functionality described as being carried out by one or more components discussed above or instructions for implementing one or more of the methods described above. The processor 1002 may access the memory 1004 by way of a system bus 1006. In addition to storing executable instructions, the memory 1004 may also store energy spectrums corresponding to various materials/elements.

The computing device 1000 additionally includes a data store 1008 that is accessible by the processor 1002 by way of the system bus 1006. The data store 1008 may include executable instructions, observed energy spectrums, etc. The computing device 1000 also includes an input interface 1010 that allows external devices to communicate with the computing device 1000. For instance, the input interface 1010 may be used to receive instructions from an external computer device, from a user, etc. The computing device 1000 also includes an output interface 1012 that interfaces the computing device 1000 with one or more external devices. For example, the computing device 1000 may display text, images, etc. by way of the output interface 1012.

Additionally, while illustrated as a single system, it is to be understood that the computing device 1000 may be a distributed system. Thus, for instance, several devices may be in communication by way of a network connection and may collectively perform tasks described as being performed by the computing device 1000.

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and Blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Alternatively, or in addition, the functionally described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the details description or the claims, such term is intended to be inclusive in a manner similar to the term "comprising" as "comprising" is interpreted when employed as a transitional word in a claim.

What is claimed is:

1. A system that facilitates identifying elemental composition of a sample, the system comprising:
    a mono-energetic neutron source that emits neutrons having known energies;
    a first detector unit that detects a neutron emitted from the mono-energetic neutron source, the first detector unit outputting a first electrical signal responsive to detecting the neutron;
    a second detector unit that detects the neutron subsequent to the first detector unit detecting the neutron, the second detector unit outputting a second electrical signal responsive to detecting the neutron, the sample positioned between the first detector unit and the second detector unit; and
    at least one electronic circuit that is configured to identify at least one element in the sample based upon an energy-dependent attenuation of neutrons caused by presence of the sample between the first detector unit and the second detector unit.

2. The system of claim 1, further comprising a plurality of detector units positioned about the sample, the plurality of detector units positioned to detect neutrons that are first detected by the first detector unit.

3. The system of claim 1, wherein the energy of the neutron is downscattered responsive to impacting a scintillator of the first detector unit.

4. The system of claim 3, wherein the first detector unit is configured to downscatter neutrons that impact the scintillator of the first detector unit over a range of energies, wherein neutrons that exit the first detector unit have energies between 1 MeV and 13 MeV.

5. The system of claim 1, the energy dependent attenuation of the neutrons computed based upon known position of the first detector unit relative to the second detector unit or a time of flight of the neutron between the first detector unit and the second detector unit.

6. The system of claim 1, the at least one circuit further configured to generate a volumetric image of the sample based upon the energy dependent attenuation of the neutrons.

7. The system of claim 1, further comprising a first group of detector units and a second group of detector units, the first detector unit included in the first group of detector units and the second detector unit included in the second group of detector units.

8. The system of claim 1, wherein a distance between the first detector unit and the second detector unit is known, and wherein the at least one electronic circuit identifies the at least one element in the sample based upon the distance between the first detector unit and the second detector unit.

9. The system of claim 1, the at least one electronic circuit further configured to:
    assign a first time tag to the neutron responsive to the first detector unit detecting the neutron;
    set a time window based upon the first time tag; and
    assign a second time tag to the neutron only if the at least one electronic circuit receives the second electrical signal in the time window.

10. The system of claim 1, wherein the element is one of hydrogen, oxygen, carbon, or nitrogen.

11. The system of claim 1, wherein the at least one electronic circuit is configured to identify that the material is associated with an explosive or an illicit drug.

12. A method comprising:
    receiving a first signal from a first detector unit, the first signal indicating that a neutron emitted from a mono-energetic neutron has impacted a scintillator of the first detector unit;
    receiving a second signal from a second detector unit, the second signal indicating that the neutron has impacted a scintillator of the first detector unit subsequent to exiting the first detector unit; and
    identifying that a sample positioned between the first detector unit and the second detector unit comprises a particular element based upon the first signal and the second signal.

13. The method of claim 12, wherein identifying that the sample comprises the particular element comprises computing energy dependent attenuation of neutrons over multiple travel paths through the sample, the energy dependent attenuation caused by the neutrons passing through the sample.

14. The method of claim 13, wherein the energy dependent attenuation of the neutrons is computed based upon a time of flight of the neutron when travelling between the first detector unit and the second detector unit.

15. The method of claim 13, wherein the energy dependent attenuation of the neutrons is computed based upon a known position of the mono-energetic neutron generator, a known position of the first detector unit, and a known position of the second detector unit.

16. The method of claim 12, further comprising:
    responsive to receiving the first electrical signal, assigning a first time tag to the neutron; and
    identifying a time window based upon the first time tag, the second electrical signal received in the time window.

17. The method of claim 16, further comprising assigning a second time tag to the neutron responsive to receiving the second electrical signal, wherein the particular element is identified based upon the first time tag and the second time tag.

18. The method of claim 12, further comprising identifying that the sample is an explosive based upon the sample comprising the particular element.

19. The method of claim 12, further comprising generating a volumetric image of the sample based upon the first electrical signal and the second electrical signal, the volumetric image indicating spatial distribution of the particular element in the sample.

20. A system comprising:
    a mono-energetic neutron generator; and
    a plurality of detector units arranged in a circle about a sample, the plurality of detector units comprising a first group of detector units and a second group of detector units, the mono-energetic neutron generator positioned on an exterior of the circle, wherein detector units in the first group of detector units are configured to detect and downscatter, in energy, neutrons emitted from the mono-energetic neutron generator, and detector units in the second group of detector units are configured to detect neutrons downscattered in energy by the detector units in the first group of detector units.

* * * * *